United States Patent
Lee et al.

(10) Patent No.: US 7,396,399 B2
(45) Date of Patent: Jul. 8, 2008

(54) BIPYRIDINE-BASED METAL COMPLEX AND INK COMPOSITION COMPRISING THE SAME

(75) Inventors: Jong-in Lee, Suwon-si (KR); Seung-min Ryu, Yongin-si (KR); Su-aa Jung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 530 days.

(21) Appl. No.: 10/902,890

(22) Filed: Aug. 2, 2004

(65) Prior Publication Data
US 2005/0033053 A1     Feb. 10, 2005

(30) Foreign Application Priority Data
Aug. 8, 2003    (KR) ................. 10-2003-0055021

(51) Int. Cl.
*C09D 11/00*    (2006.01)
*C07F 1/08*     (2006.01)
*C07D 471/02*   (2006.01)
(52) U.S. Cl. .............. 106/31.47; 546/10; 546/88
(58) Field of Classification Search .............. 546/10, 546/88; 106/31.47
See application file for complete search history.

(56) References Cited

U.S. PATENT DOCUMENTS

| | | | |
|---|---|---|---|
| 3,670,021 A | * | 6/1972 | Goetz et al. ............ 564/126 |
| 3,971,739 A | | 7/1976 | McCrae et al. |
| 3,987,023 A | | 10/1976 | McCrae et al. |
| 4,077,953 A | | 3/1978 | McCrae et al. |
| 4,152,324 A | | 5/1979 | McCrae et al. |
| 4,424,359 A | | 1/1984 | Kaschig et al. |
| 5,104,988 A | | 4/1992 | Ohkawa |

FOREIGN PATENT DOCUMENTS

| | | | |
|---|---|---|---|
| DE | 1251954 | * | 10/1967 |
| JP | 2000-100482 | | 4/2000 |
| JP | 2001-152044 | | 6/2001 |
| JP | 2002-241634 | | 8/2002 |

OTHER PUBLICATIONS

Majima, E. et al.: Close location of the first loop to the third loop of the mitochondrial ADP/ATP carrier deduced from cross-linking catalyzed by copper-o-phenanthroline of the solubilized carrier with triton X-100. J. Biochem. vol. 131, pp. 461-468, 2002.*
Korean Office Action dated Aug. 26, 2005, corresponds to Korean Office Action 2003-0055021.

* cited by examiner

*Primary Examiner*—Charanjit S Aulakh
(74) *Attorney, Agent, or Firm*—Staas & Halsey LLP

(57) ABSTRACT

A bipyridine-based metal complex includes a complex of bipyridine-based ligands and metals, and is utilized in an ink composition. The bipyridine-based metal complex may be used alone, as well as in combination with other coloring agents.

8 Claims, No Drawings

BIPYRIDINE-BASED METAL COMPLEX AND INK COMPOSITION COMPRISING THE SAME

CROSS-REFERENCE TO RELATED APPLICATIONS

This application claims the priority of Korean Patent Application No. 2003-55021, filed on Aug. 8, 2003, in the Korean Intellectual Property Office, the disclosure of which is incorporated herein in its entirety by reference.

BACKGROUND OF THE INVENTION

1. Field of the Invention

The present invention relates to a bipyridine-based metal complex and an ink composition comprising the same, and more particularly, to a bipyridine-based metal complex in which metal is coordinated with bipyridine-based ligands having superior coloring ability and durability, and an ink composition comprising the complex as a coloring agent.

2. Description of the Related Art

In general, coloring agents embody their inherent colors by selectively absorbing or reflecting visible light, and are classified as dyestuffs and pigments.

Dyestuffs are used in any materials to be dyed, thus providing considerable fastness to daylight, washing, friction, and the like. Pigments are coloring matters in the form of particulates, and are not absorbed into the material to be dyed but adhere to the surface of the material to be dyed by physical means (e.g., adhesion, and the like), thus providing their inherent colors.

Dyestuffs are used as coloring agents in fibers, leathers, furs, papers, foodstuffs, t medicines, cosmetics, ink-jet inks, and the like, and pigments are used in paints, printing ink, plastics, rubber, furniture manufacturing, textiles, papers, cosmetics, ceramics, and the like.

The colors embodied by the coloring agents are determined by the wavelengths in the visible light range of 3,000 to 7,000 Å selectively reflected or transmitted by the particles of the coloring agent. The coloring agents may be classified into organic coloring agents and inorganic coloring agents based on their molecular structures. In the organic coloring agents, the colors are embodied by cycles of absorbing, transferring and transmitting light through conjugation of double bonds, and in the inorganic coloring agents, the colors are embodied by the ligands coordinated with metals in the compounds absorbing light, thus putting the ligand-metal complex in an excited energy state, and then emitting light by lowering to base energy level.

In general, organic coloring agents may embody a wide range of colors, and their colors are bright and clear, but they have problems of weak light resistance causing decoloration or discoloration. On the other hand, inorganic coloring agents are very durable and have good light resistance, but embody a narrow range of colors and have limited classes.

Various coloring agent compounds, for example, pigment complex compounds, employing metal complexes are disclosed in U.S. Pat. Nos. 3,971,739, 3,987,023, 4,077,953, 4,152,324, and Japanese Unexamined Patent Application No. 2001-152044. These patents disclose methods in which a metal is incorporated into an azo group containing compound to form a complex compound by forming covalent bonds using intramolecular coordinate bonds.

However, in such methods, the compounds should comprise a specific functional group of an azo group, and the compounds should comprise both a coordinate bond functional group and a covalent bond functional group within molecules such that coordinate bonds and covalent bonds are formed at proper distances when reacting with metal compounds. Also, the above disclosed complex compounds are not satisfactorily durable and cannot embody a wide range of colors, and the like. Thus, there remains a need for improvements in the compounds.

SUMMARY OF THE INVENTION

The present invention provides a bipyridine-based metal complex having improved durability and the ability to embody colors, and an ink composition comprising the same and having effective storage stability, light resistance and abrasion resistance.

According to an aspect of the present invention, a bipyridine-based metal complex may be represented by formula (I):

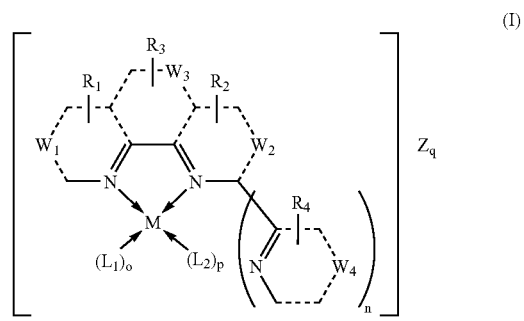

wherein $W_1$, $W_2$ and $W_4$ are each an atom included in a 4 to 8-membered heteroaryl group or a heterocycloalkenyl group;

$W_3$ is an atom included in a 0 to 8-membered group selected from the group consisting of a cycloalkyl group, a cycloalkenyl group, an aryl group, a heteroaryl group, a heterocycloalkyl group and a heterocycloalkenyl group;

n is an integer of 0 to 100;

$R_1$, $R_2$, $R_3$ and $R_4$ are respectively mono-substituents, or the same or different multi-substituents, and are each selected from the group consisting of a hydrogen atom, a halogen atom, a nitro group, —$SO_3H$, —COOH, a substituted or unsubstituted $C_1$-$C_{20}$ alkyl group, a substituted or unsubstituted $C_1$-$C_{20}$ heteroalkyl group, a hydroxy group, an amino group, a cyano group, a substituted or unsubstituted $C_2$-$C_{20}$ alkenyl group, a substituted or unsubstituted $C_1$-$C_{20}$ alkoxy group, a substituted or unsubstituted $C_1$-$C_{20}$ alkyl sulfonamide group, a substituted or unsubstituted $C_6$-$C_{20}$ aryl sulfonamide group, a substituted or unsubstituted $C_1$-$C_{20}$ acylamino group, a $C_1$-$C_{20}$ alkylureido group, a $C_6$-$C_{20}$ arylureido group, a $C_2$-$C_{20}$ alkoxycarbonyl group, a $C_2$-$C_{20}$ alkoxycarbonylamino group, a carbamoyl group, a sulfamoyl group, a sulfo group or its salt, a carboxy group or its salt, a substituted or unsubstituted $C_1$-$C_{20}$ hydroxyalkyloxyalkyl group, a substituted or unsubstituted $C_1$-$C_{20}$ dialkylaminoalkyl group, a substituted or unsubstituted $C_6$-$C_{20}$ pyridylalkyl group, a substituted or unsubstituted $C_5$-$C_{20}$ pyridyl group, a substituted or unsubstituted $C_6$-$C_{20}$ imidazolyl group, a hydrazine group, a hydrozone group, a substituted or unsubstituted $C_1$-$C_{20}$ pyridylalkyl group, a substituted or unsubstituted $C_6$-$C_{20}$ aryl group, a substituted or unsubstituted $C_6$-$C_{20}$ arylalkyl group, a substituted or unsubstituted $C_6$-$C_{20}$ heteroaryl group, or $C_6$-$C_{20}$ heteroarylalkyl group, a substituted or unsubstituted $C_6$-$C_{20}$ heteroarylalkenyl group, and a substituted or Unsubstituted $C_3$-$C_{20}$ heterocycloalkyl group;

M is a metal atom of one of groups III to XIV;

$L_1$ is an anionic ligand;

$L_2$ is a neutral ligand;

Z is a counter ion; and o, p and q are each integers of 0 to 10, wherein o and p are not equal to zero simultaneously.

According to another aspect of the present invention, a bipyridine-based metal complex may be represented by formula (I):

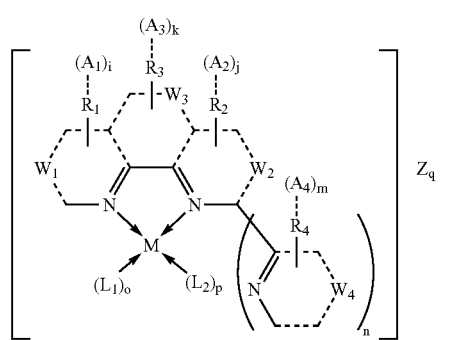

(II)

wherein $W_1$, $W_2$ and $W_4$ are each an atom included in a 4 to 8-membered heteroaryl group or heterocycloalkenyl group;

$W_3$ is an atom included in a 0 to 8-membered group selected from the group consisting of a cycloalkyl group, a cycloalkenyl group, an aryl group, a heteroaryl group, a heterocycloalkyl group and a heterocycloalkenyl group;

n is an integer of 0 to 100;

$A_1$, $A_2$, $A_3$ and $A_4$ represent the same or different coloring agents, and are capable of binding, respectively, to at least one of $W_1$, $W_2$, $W_3$ and $W_4$;

i, j, k and m are each independently 0 or 1 such that i, j, k and m are not all equal to zero;

when i, j, k and m are each equal to 1, $R_1$, $R_2$, $R_3$ and $R_4$ are linkers;

when i is zero, $R_1$ is a mono-substituent, or the same or different multi-substituents, and each is selected from the group consisting of a hydrogen atom, a halogen atom, a nitro group, —$SO_3H$, —COOH, a substituted or unsubstituted $C_1$-$C_{20}$ alkyl group, a substituted or unsubstituted $C_1$-$C_{20}$ heteroalkyl group, a hydroxy group, an amino group, a cyano group, a substituted or unsubstituted $C_2$-$C_{20}$ alkenyl group, a substituted or unsubstituted $C_1$-$C_{20}$ alkoxy group, a substituted or unsubstituted $C_1$-$C_{20}$ alkyl sulfonamide group, a substituted or unsubstituted $C_6$-$C_{20}$ aryl sulfonamide group, a substituted or unsubstituted $C_1$-$C_{20}$ acylamino group, a $C_1$-$C_{20}$ alkylureido group, a $C_6$-$C_{20}$ arylureido group, a $C_2$-$C_{20}$ alkoxycarbonyl group, a $C_2$-$C_{20}$ alkoxycarbonylamino group, a carbamoyl group, a sulfamoyl group, a sulfo group or its salt, a carboxy group or its salt, a substituted or unsubstituted $C_1$-$C_{20}$ hydroxyalkyloxyalkyl group, a substituted or unsubstituted $C_1$-$C_{20}$ dialkylaminoalkyl group, a substituted or unsubstituted $C_6$-$C_{20}$ pyridylalkyl group, a substituted or unsubstituted $C_5$-$C_{20}$ pyridyl group, a substituted or unsubstituted $C_6$-$C_{20}$ imidazolyl group, a hydrazine group, a hydrozone group, a substituted or unsubstituted $C_1$-$C_{20}$ pyridylalkyl group, a substituted or unsubstituted $C_6$-$C_{20}$ aryl group, a substituted or unsubstituted $C_6$-$C_{20}$ arylalkyl group, a substituted or unsubstituted $C_6$-$C_{20}$ heteroaryl group, $C_6$-$C_{20}$ heteroarylalkyl group, a substituted or unsubstituted $C_6$-$C_{20}$ heteroarylalkenyl group, and a substituted or unsubstituted $C_3$-$C_{20}$ heterocycloalkyl group;

when j is zero, $R_2$ is selected from the group recited for the $R_1$ where i is zero;

when k is zero, $R_3$ is selected from the group recited for the $R_1$ where i is zero;

when m is zero, $R_4$ is selected from the group recited for the $R_1$ where i is zero;

M is a metal atom of one of groups III to XIV;

$L_1$ is an anionic ligand;

$L_2$ is a neutral ligand;

Z is a counter ion; and o, p and q are each integers of 0 to 10, wherein o and p are not equal to zero simultaneously.

In formula (II) above, the linker of $R_1$, $R_2$, $R_3$ and $R_4$ is a linker selected from the group consisting of —O—, —C(=O)O-M NH—, —C(=O)NH— and —CH=N—.

In formula (I), at least one of $R_1$, $R_2$, $R_3$ and $R_4$ may be preferably selected from the group consisting of —OH, —$NH_2$, —COOH, —$SO_3H$, —$NO_2$, —F, —Cl, —Br and —I.

According to another aspect of the present invention, an ink composition comprises one of the bipyridine-based metal complexes of formulas (I) and (II), and an aqueous liquid medium. The ink composition may include 0.1 to 10 parts by weight of the bipyridine-based metal complex per 100 parts by weight of the aqueous liquid medium.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

A metal complex including compounds having a bipyridine-based structure according to an embodiment of the present invention, represented by formula (I) or (II), functions as a coloring agent. Even if the compounds do not have bipyridine-based structures, it is possible to use the metal complex as a coloring agent by incorporating bipyridine ligands into desired compounds through general reactions so that complexation occurs, or by incorporating the compounds having bipyridine-based structures into the functional groups generally contained in the surface of another existing coloring agent through a mild reaction, then coordinately binding metal with bipyridine-based ligands.

At least one of $R_1$, $R_2$, $R_3$ and $R_4$ in the bipyridine-based metal complex of formula (I) may have substituent groups that may react with coloring agents. Non-limiting examples of such substituent groups include —OH, —$NH_2$, —COOH, —$SO_3H$, —$NO_2$, —F, —Cl, —Br, —I, and the like. Such functional groups react with —COOH, —OH, —CO—, —COH, —$NH_2$, and the like, which are generally contained in existing coloring agents.

In formulas (I) and (II), n represents the number of pyridine moieties connected to the backbone of bipyridine-based compounds, is between 0 and 100, and may be between 0 and 10.

In formulas (I) and (II), M is a coordinately bound metal having a positive charge of +1 to +5. The anionic ligand $L_1$ may have a negative charge of −1 to −6, and the counter ion Z may have a charge of −2 to +2.

M is a metal of one of Groups III to XIV, and may be silver (Ag), aluminum (Al), gold (Au), cerium (Ce), cobalt (Co), chromium (Cr), copper (Cu), europium (Eu), iron (Fe), germanium (Ge), indium (In), lanthanum (La), manganese (Mn), nickel (Ni), palladium (Pd), platinum (Pt), rhodium (Rd), ruthenium (Ru), scandium (Sc), silicon (Si), samarium (Sm), titanium (Ti), uranium (U), zinc (Zn), zirconium (Zr), or the like.

As used herein, the term "anionic ligand" refers to a ligand having a negative charge before binding to the metal M, and the term "neutral ligand" refers to a ligand having a neutral charge before binding to the metal.

The anionic ligand $L_1$ has a negative charge of −1 to −6, and may be a halogen atom ion (F−, Cl−, Br−, I−), R—NO$_3$* (R is a $C_1$-$C_{20}$ alkyl, a $C_6$-$C_{20}$ aryl, or a $C_2$-$C_{20}$ heteroaryl), a $C_1$-$C_{10}$ alkylcarboxylate ion (e.g., acetate, trifluoroacetate), RCN* (R is a $C_1$-$C_{20}$ alkyl, a $C_6$-$C_{20}$ aryl, a $C_2$-$C_{20}$ heteroaryl, or —(CH$_2$CH$_2$O)$_z$— (Z is a number of 1 to 50), ROO* (R is a $C_1$-$C_{20}$ alkyl, a $C_6$-$C_{20}$ aryl, or a $C_2$-$C_{20}$ heteroaryl), RO* (R is a $C_1$-$C_{20}$ alkyl, a $C_6$-$C_{20}$ aryl, or a $C_2$-$C_{20}$ heteroaryl), RSCN* (R is a $C_1$-$C_{20}$ alkyl, a $C_6$-$C_{20}$ aryl, or a $C_2$-$C_{20}$ heteroaryl), RN$_3$* (R is a $C_1$-$C_{20}$ alkyl, a $C_6$-$C_{20}$ aryl, or a $C_2$-$C_{20}$ heteroaryl), RCO$_3$* (R is a $C_1$-$C_{20}$ alkyl, a $C_6$-$C_{20}$ aryl, or a $C_2$-$C_{20}$ heteroaryl), RSO$_4$* (R is a $C_1$-$C_{20}$ alkyl, a $C_6$-$C_{20}$ aryl, or a $C_2$-$C_{20}$ heteroaryl) or the group represented by the following structural formulas (R" is a $C_1$-$C_{20}$ alkylene, a $C_6$-$C_{20}$ arylene, or a $C_2$-$C_{20}$ heteroarylene) wherein the * represents the position at which the anionic ligand $L_1$ binds to M.

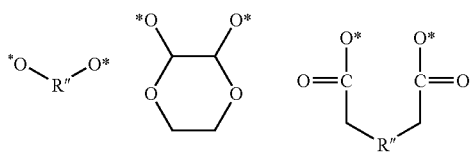

In the present embodiment, the $L_1$ binds to the M to become hydrophobic.

The neutral ligand $L_2$ may be a monodentate ligand, a didentate ligand, a tridentate ligand, or the like, such as ammonia, water, triphenylphosphine, *NH$_2$RNH$_2$* (R is a $C_1$-$C_{20}$ alkylene, a $C_6$-$C_{20}$ arylene, or a $C_2$-$C_{20}$ heteroarylene), 2,2'-bipyridine, 1,10-phenanthroline, 2,2',2"-terpyridine, and the group represented by the structural formula;

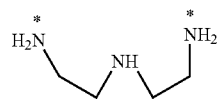

Neutral $L_2$ used in the present embodiment may bind to the M to become hydrophobic.

To make a complex ion neutral, a positive ion or a negative ion is used as the counter ion Z. The counter ion Z may have a charge of −2 to 2. When the counter ion Z is a negative ion, it may be a halide ion (e.g., F—, Cl—, Br—, I—), a sulfite ion, a $C_1$-$C_{10}$ alkyl sulfite ion, a sulfate ion, a $C_1$-$C_{10}$ alkyl sulfate ion, a nitrate ion, a nitrite ion, a perchloric acid ion, a $C_1$-$C_{10}$ alkylcarboxylate ion, a salicylate ion, a benzoate ion, a hexafluorophosphate ion, or a tetrafluoroborate ion. When the counter ion Z is a positive ion, it may be lithium (univalent), sodium (univalent), potassium (univalent), ammonium (univalent), or phosphonium (univalent).

When preparing the bipyridine-based metal complex represented by formula (I) or (II), the compounds used for providing the metal (M) ion may be one of zinc chloride, zinc sulfate, zinc nitrate, zinc acetate, nickel chloride (II), nickel sulfate (II), nickel nitrate (II), nickel acetate (II), nickel stearylate (II), bis(2,4-pentanedionato)diaquanickel (II), bis (dimethylglyoxymato) nickel (II), bis(3-methoxycarbonyl-2, 4-tetodecanedionato)nickel (II), tris(glycineamido) nickel (II), tetraphenyl borate, cobalt hexamine (III) chlorinated product, tris(ethylenediamine) cobalt (III) chlorinated product, cis-dichlorotetraammine cobalt (III) chlorinated product, ammonium tetranitrodiamine cobalt (III) acid, potassium hexacyano cobalt (III) acid, copper chloride (II), copper tetrafluoroborate (II), bis(ethylenediamine) copper (II) sulfate, rhodium chloride (II), rhodium sulfate (II), dirhodium tetraacetic acid (II), hexaamine rhodium (III) chloride, potassium hexacyanorhodium (III), ruthenium bromide (III), hexaammine ruthenium (III) bromide, potassium hexacyano ruthenium (II) acid, palladium sulfate (II), ammonium acid of tetrachloro palladium (II), tetraammine palladium (II) chloride, tetraammine platinum (II) chloride, bisethylendiamine platinum (II) chloride, hexaammine platinum (IV) chloride), tris(ethylenediamine) platinum (IV) chloride, or the like.

Besides metals, the ligand backbone of formula (I), when n is zero and does not include a $W_3$ ring, is represented by formula (III). Compounds given by formula (III) are derivatives that include 2,2'-bipyridine, i.e., a ligand capable of forming a complex with a metal, as a backbone, and may be used as a coloring agent embodying its inherent colors.

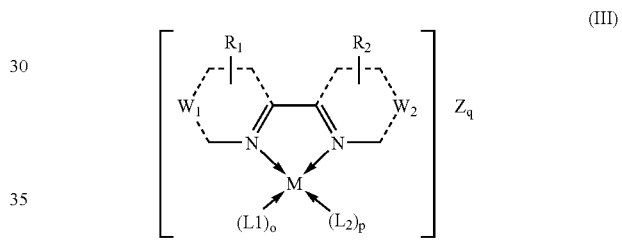

In formula (III), $W_1$ and $W_2$ are each atoms included in a 4 to 8-membered ring of a heteroaryl group or a heterocycloalkenyl group, and M, Z, $L_1$, $L_2$, o, p, q, $R_1$ and $R_2$ are described above.

According to another embodiment of the present invention, 2,2'-bipyridine group may be incorporated into the coloring agents through a general reaction with another existing coloring agent.

The following reaction scheme I illustrates a reaction between carboxyl group containing compounds of 2,2'-bipyridine derivatives and coloring agents.

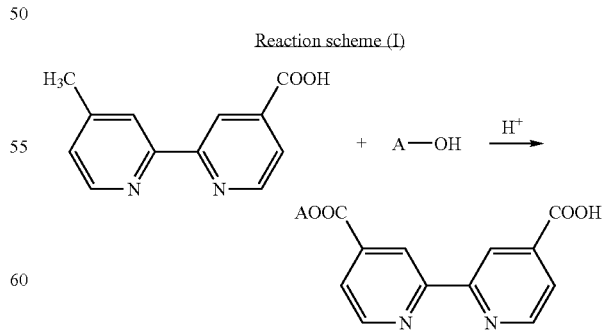

In reaction scheme (I) above, A-OH is a coloring agent, and the starting materials of the reaction are ones in which $W_1$ and $W_2$ of the formula (III) are 6-membered rings of a heteroayl group. An ester compound, the product of the reaction scheme 1, is produced through an ester reaction of a —COOH group of the 2,2'-bipyridine derivative with an —OH group contained in coloring agents. That is, the structure of the 2,2'-bipyridine derivative, i.e., the ligand capable of coordinately binding with a metal, is incorporated into the coloring agents which do not have the structure of the 2,2'-bipyridine derivative through the general ester reaction.

Also besides metal, the ligand backbone of formula (I) may be a compound represented by formula (IV) below. The compound is a 1,10-phenanthroline derivative, i.e., a ligand capable of forming a complex with a metal, as a backbone, and may be used as a coloring agent embodying its inherent colors.

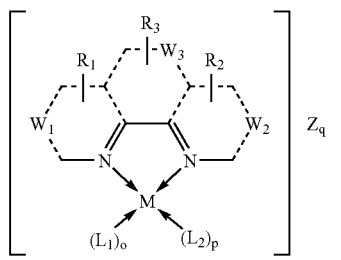

In formula (IV), $W_1$, $W_2$, $W_3$, M, Z, $L_1$, $L_2$, o, p, q, $R_1$, $R_2$ and $R_3$ are as described above.

Reaction scheme (II) below illustrates an example of a binding reaction between a coloring agent having a carboxyl group and a 1,10-phenanthroline derivative represented by formula (IV).

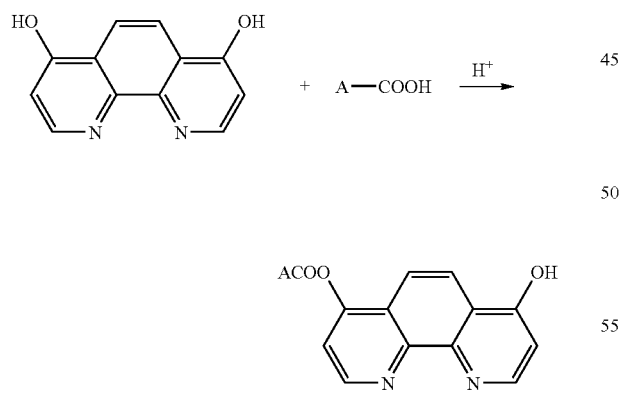

An ester compound, the product of reaction scheme (II), is produced through an ester reaction of an —OH group of the 1,10-phenanthroline derivative with a —COOH group contained in the coloring agents.

Also besides metal, the ligand backbone of formula (I) may be a compound represented by formula (V) below. The compound is a derivative including a 2,2',6',2"-terpyridine derivative, i.e., a ligand capable of forming a complex with a metal, as a backbone, and may also be used as a coloring agent.

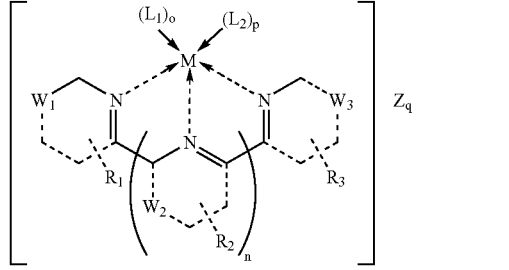

In formula (V) above, $W_1$, $W_2$, $W_3$, M, Z, $L_1$, $L_2$, o, p, q, $R_1$, $R_2$, n and $R_3$ are as described above.

Reaction scheme (III) illustrates an example of a reaction in which a chlorine group containing a compound of a 2,2':6',2"-terpyridine derivative represented by the formula (V) binds to coloring agents.

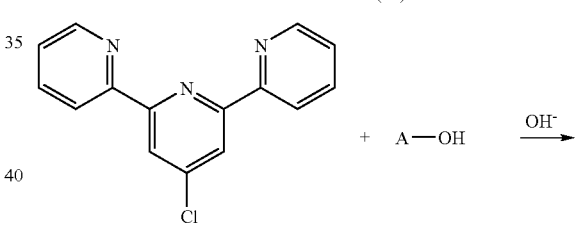

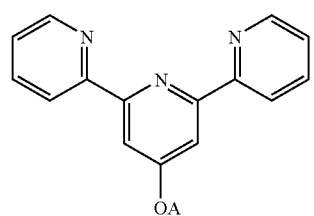

According to the reaction, the —Cl group of the 2,2':6',2"-terpyridine derivative causes nucleophilic aromatic substitution with an —OH contained in coloring agents to produce ether compounds.

According to embodiments of the present invention, compounds may be represented by formulas (VI) through (XIII) below, which are specific examples of the bipyridine-based metal complex represented by formula (I).

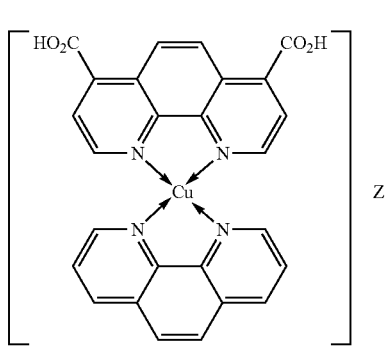

(VI)

In formula (VI), Z is a counter ion selected from among $(CH_3COO)_2$, $(SO_4)_2$, $(NO_3)_2$, $(CO_3)_2$, $(ClO_4)_2$, and $Cl_2$.

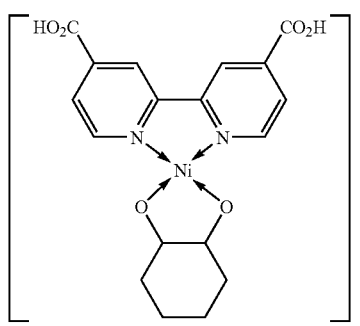

(VII)

In formula (VII), Z is a counter ion selected from $2Na^+$ and $2K^+$.

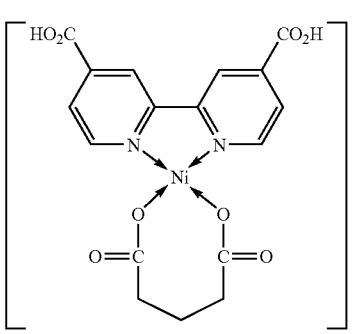

(VIII)

In formula (VIII), Z is a counter ion selected from among $(CH_3COO)_2$, $(SO_4)_2$, $(NO_3)_2$, $(CO_3)_2$, $(ClO_4)_2$, and $Cl_2$.

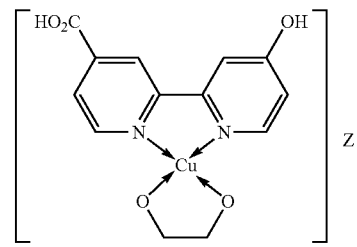

(IX)

In formula (IX), Z is a counter ion selected from among $(CH_3COO)_2$, $(SO_4)_2$, $(NO_3)_2$, $(CO_3)_2$, $(ClO_4)_2$, and $Cl_2$.

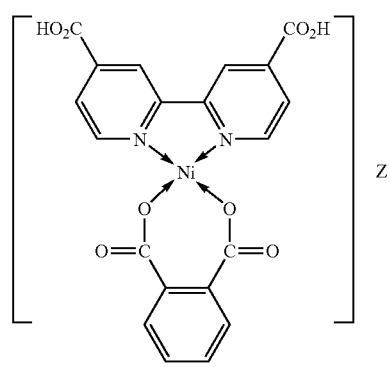

(X)

In formula (X), Z is a counter ion selected from among $(CH_3COO)_2$, $(SO_4)_2$, $(NO_3)_2$, $(CO_3)_2$, $(ClO_4)_2$, and $Cl_2$.

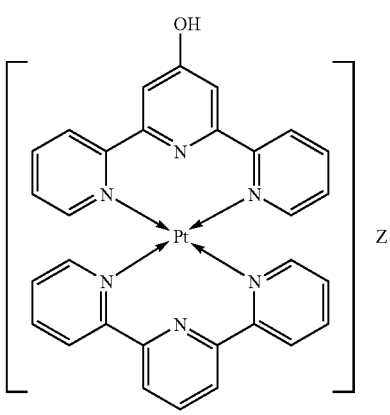

(XI)

In formula (XI), Z is a counter ion selected from among $(CH_3COO)_2$, $(SO_4)_2$, $(NO_3)_2$, $(CO_3)_2$, $(ClO_4)_2$, and $Cl_2$.

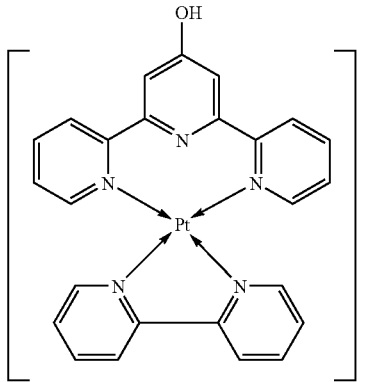

(XII)

In formula (XII), Z is a counter ion selected from among $(CH_3COO)_2$, $(SO_4)_2$, $(NO_3)_2$, $(CO_3)_2$, $(ClO_4)_2$, and $Cl_2$.

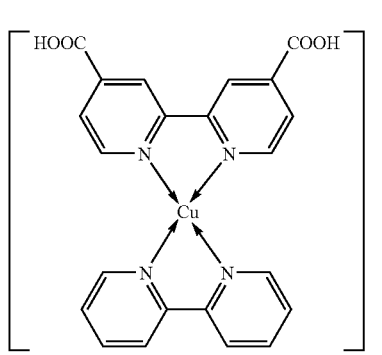

(XIII)

In formula (XIII), Z is a counter ion selected from among $(CH_3COO)_2$, $(SO_4)_2$, $(NO_3)_2$, $(CO_3)_2$, $(ClO_4)_2$, and $Cl_2$.

Meanwhile, in the bipyridine-based coloring compound represented by formula (II), A represents a coloring agent, either an organic or an inorganic coloring agent. Coloring agents capable of reacting with bipyridine-based ligands include dyestuffs and pigments, and are not limited to the following.

Specific examples of dyestuffs include C.I. DIRECT BLACK 9, 17, 19, 22, 32, 56, 91, 94, 97, 166, 168, 174, 199, C.I. DIRECT BLUE 1, 10, 15, 22, 77, 78, 80, 200, 201, 202, 203, 207, 211, C.I. DIRECT RED 2, 4, 9, 23, 31, 39, 63, 72, 83, 84, 89, 111, 173, 184, 240, C.I. DIRECT YELLOW 8, 9, 11, 12, 27, 28, 29, 33, 35, 39, 41, 44, 50, 53, 58, and the like, and specific examples of pigments include carbon black, graphite, vitreous carbon, activated charcoal, activated carbon, anthraquinone, phthalocyanine blue, phthalocyanine green, diazos, monoazos, pyranthrones, perylene, quinacridone, indigoid pigments, and the like.

Coloring agents produced by binding a bipyridine-based ligand-metal complex to the coloring agents may be variously used in fibers, leathers, furs, papers, foodstuffs, medicines, cosmetics, ink-jet inks, printing ink, paints, printing inks, plastic coloration, rubber coloration, furniture manufacturing, textile printing, paper manufacturing, cosmetics manufacturing, ceramic industry, and the like. In formulas (I) and (III), a carbon number of the heteroaryl group is 2 to 20, and a carbon number of the heterocycloalkeyl group is 2 to 20.

In formulas (I) through (III), a carbon number of the heteroaryl group is 2 to 20, and a carbon number of the heterocycloalkenyl group is 2 to 20.

In formulas (I) and (II), the unsubstituted $C_1$-$C_{20}$ alkyl may be methyl, ethyl, propyl, isobutyl, sec-butyl, pentyl, iso-amyl, hexyl, and the like, in which at least one of the hydrogen atoms may be substituted with a halogen atom, a hydroxy group, a nitro group, a cyano group, an amino group, an amidino group, a hydrazine, a hydrazone, a carboxyl group or its salt, a sulfonic acid group or its salt, a phosphoric acid group or its salt, a $C_1$-$C_{20}$ alkyl, a $C_2$-$C_{20}$ alkenyl, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl.

The term "unsubstituted $C_2$-$C_{20}$ alkenyl group" used herein refers to the group that contains a carbon double bond at the middle or distal end of an alkyl group as described above. The unsubstituted $C_1$-$C_{30}$ alkenyl group may be one of ethylene, propylene, butylenes, hexylene, or the like. At least one of the hydrogen atoms in the alkenyl group may be substituted with the same substituents as the above-mentioned alkyl groups.

The term "heteroalkyl group" used herein refers to one of the alkyl groups as described above containing a nitrogen atom, a sulfur atom, an oxygen atom or a phosphorus atom. The heteroalkyl group may be one of methoxy, ethoxy, propoxy, butoxy and t-butoxy, or the like, and examples of the group containing substituents include haloalkoxy radicals such as fluoromethoxy, chlroromethoxy, trifluoromethoxy, trifluoroethoxy, fluoroethoxy and fluroropropoxy. At least one of the hydrogen atoms in the heteroalkyl group may be substituted with the same substituents as the above-mentioned alkyl group.

The term "aryl group" used herein refers to a $C_6$-$C_{20}$ carbocyclic aromatic system containing at least one ring, used alone or in combination, wherein the rings may be attached or fused together in a pendant manner. The term "aryl" refers to aromatic radicals such as phenyl, naphthyl or tetrahydronaphthyl. The aryl group may contain substituents such as haloalkylene, nitro, cyano, alkoxy and lower alkylamiNo. Also, at least one of the hydrogen atoms in the aryl group may be substituted with the same substituents as the above-mentioned alkyl group.

The term "arylalkyl group" used herein refers to the group wherein part of the hydrogen atoms in the arylene groups as described above is substituted with a radical such as a lower alkyl, for example, methyl, ethyl, propyl, or the like. The arylalkyl group may be one of benzyl, phenylethyl, or the like. At least one of the hydrogen atoms in the arylalkyl groups may be substituted with the same substituents as the above-mentioned alkyl group.

The term "heteroaryl group" used herein refers to monovalent monocyclic or bivalent bicyclic aromatic organic compounds including a $C_2$-$C_{20}$ ring, and 1, 2 or 3 heteroatoms selected from N, O, P or S, and C as a remaining ring atom. At least one of the hydrogen atoms in the heteroatoms may be substituted with the same substituents as the above-mentioned alkyl group.

The term "heteroarylalkyl group" as used herein refers to the group wherein some of the hydrogen atoms in the heteroaryl group as described above are substituted with alkyl groups. At least one of the hydrogen atoms in the heteroarylalkyl groups may be substituted with the same substituents as the above-mentioned alkyl group.

Hereinafter, the ink composition comprising a bipyridine-based metal complex represented by above-mentioned formula (I) or (II) will be described in detail.

An ink composition according to an embodiment of the invention comprises an aqueous liquid medium and a coloring agent. The coloring agent may be a bipyridine-based metal complex represented by the above-mentioned formula (I) or (II) used alone or in combination with a coloring agent, such as a general dyestuff, pigment, or the like. The ink composition includes 0.1 to 10 parts by weight of the bipyridine-based metal complex represented by above-mentioned formula (I) or (II) based on 100 parts by weight of the aqueous liquid medium. If the bipyridine-based metal complex represented by formula (I) or (II) exceeds 10 parts per weight, storage stability is decreased, and if the amount of the bipyridine-based metal complex is less than 0.1 parts per weight, durability is not affected. Thus, such conditions are not preferable. If the bipyridine-based metal complex represented by formula (I) or (II) combined with a general coloring agent is used as a coloring agent when preparing an ink composition, the ink composition includes 1 to 10,000 parts by weight of a general coloring agent based on 100 parts by weight of the bipyridine-based metal complex represented by formula (I) or (II).

The aqueous liquid medium may be water used alone or in combination with at least one organic solvent. The ink composition may include 0.5 to 50 parts by weight of the organic solvent based on 100 parts by weight of solid contents. Solid contents in the ink composition refer to coloring agents when additives are not added, and both additives and coloring agents when additives are added. The viscosity and surface tension of the ink composition may be controlled by combined use of an organic solvent and an aqueous liquid medium.

The organic solvent may be one of a plurality of solvents such as alcohols, including methyl alcohol, ethyl alcohol, n-propyl alcohol, isoproyl alcohol, n-butyl alcohol, sec-butyl alcohol, t-butyl alcohol, isobutyl alcohol, and the like; ketones such as acetone, methylethylketone, diacetone alcohol, and the like; esters such as ethyl acetate, ethyl lactate, and the like; polyhydric alcohols such as ethylene glycol, diethylene glycol, triethylene glycol, propylene glycol, butylenes glycol, 1,4-butanediol, 1,2,4-butanetriol, 1,5-pentanediol, 1,2-hexanediol, 1,6-hexanediol, 1,2,6-hexanetriol, hexylene glycol, glycerol, glycerol ethoxylate, trimethylolpropane ethoxylate, and the like; lower alkyl ethers such as ethylene glycol monomethyl ether, ethylene glycol monoethyl ether, diethylene glycol methyl ether, diethylene glycol ethyl ether, triethylene glycol monomethyl ether, triethylene glycol monoethyl ether, and the like; N-containing compounds such as 2-pyrrolidone, N-methyl-2-pyrrolidone, caprolactam, and the like; and dimethyl sulfoxide, tetramethylene sulfone, thioglycol, and the like.

The ink composition may further comprise additives such as dispersing agents, viscosity controllers, surfactants, metal oxides, and materials having a hygroscopic function or stabilizing coloring agents. The ink composition may include 0.5 to 30 parts by weight of additives based on 100 parts by weight of coloring agents.

The surfactants of the ink composition control the surface tension of the ink composition to stabilize jetting at a nozzle. The surfactants performing such a function include anionic surfactants and nonionic surfactants Viscosity controllers control viscosity to maintain smooth jetting, and a viscosity controller selected from the group consisting of polyvinyl alcohol, casein, carboxymethyl cellulose is used.

The ink composition may further comprise acids or bases. The acids or bases increase the solubility of moisturizing agents in solvents and stabilizing pigments.

In one embodiment, a method of preparing the ink composition is performed as follows. First, the bipyridine-based metal complex represented by formula (I) or (II) is added to an aqueous liquid medium, then additives such as coloring agents, viscosity controllers, surfactants, and the like are optionally added thereto and mixed. Thereafter, the mixture is sufficiently stirred with a stirrer to a homogeneous state. Then, the resulting product is filtered through a filter to obtain the ink composition.

The bipyridine-based metal complex represented by formula (I) or (II), according to an embodiment of the present invention, may be used in toner compositions, various paints, coating liquids, and the like, in addition to ink compositions, and its use is not particularly limited.

The present invention will be described in greater detail with reference to the following examples. The following examples are for illustrative purposes and are not intended to limit the scope of the invention.

In these examples, embodiments of the present invention are evaluated with respect to their characteristics in ink, and these evaluation methods may also be applied to wet toners, dry toners, paints and/or coating liquids.

PREPARATION EXAMPLE 1

A 250 ml round bottom flask was filled with 10.2 g of 2,2'-bipyridine-4,4'-dicarboxylic acid, and 11.6 g of 2-amino-5-naphthol-7-sulfonic acid (corresponding to A-OH of Reaction scheme 1) as dyestuff, together with 0.5 g of p-toluene sulfonic acid as an acid catalyst, and then reacted in 100 ml of toluene through refluxing under reduced pressure for 6 hours. Water was continuously removed from the reaction using a Dean-Stark apparatus.

Then, the reaction of the resulting mixture was halted using 0.1 N of NaOH aqueous solution, an organic layer was extracted with cyclohexane and a saturated NaCl aqueous solution, and the extract was concentrated to obtain 16.5 g of corresponding object ester compound of Reaction scheme 1.

PREPARATION EXAMPLE 2

A 250 ml flask was filled with 14.8 g of 4,7-dihydroxy-1,10-phenanthroline of Reaction scheme 11, carbon black (corresponding to A-COOH of reaction scheme (II) and 0.4 g of sulfuric acid as an acid catalyst, and then reacted in 100 ml of xylene through refluxing under reduced pressure.

Then, the reaction of the resulting mixture was halted using 0.1 N of KOH aqueous solution, and was hot filtered through a funnel in which a membrane filter paper was underlain to obtain 19.5 g of the ester compound of reaction scheme (II).

PREPARATION EXAMPLE 3

12.3 g of the product of Reaction scheme II was dissolved in 100 ml of toluene, 8.5 g of cupric acetate was added, and then result was refluxed under reduced pressure for 12 hours. Then, an organic layer was extracted with cyclohexane and a saturated NaCl aqueous solution, and the extract was concentrated to obtain 18.5 g of the complex compound represented by formula (VI).

EXAMPLE 1

4.0 g of complex compound prepared according to Preparation Example 3, 77.0 g of water, 3.0 g of isopropyl alcohol, 8.0 g of ethylene glycol, 8.0 g of glycerin were mixed and stirred sufficiently in a stirrer for more than 30 minutes to a homogeneous state. Then, the resulting product was filtered through a 0.45 μm filter to obtain an ink composition.

EXAMPLE 2-8

An ink composition was prepared according to the same method used in Example 1, except that the compounds of formulas (VII), (VIII), (IX), (X), (XI), (XII) or (XIII) were used instead of the complex compound obtained according to the Preparation Example 3.

COMPARATIVE EXAMPLE 1

An ink composition was prepared according to the same method used in Example 1, except that carbon black (RAVEN 5250, prepared by COLUMBIAN CO.) was used instead of the complex compound obtained according to the Preparation Example 3.

COMPARATIVE EXAMPLE 2

An ink composition was prepared according to the same method used in Example 1, except that carbon black (REGAL 330, prepared by CABOT CO.) was used instead of the complex compound obtained according to the above Preparation Example 3.

COMPARATIVE EXAMPLE 3

An ink composition was prepared according to the same method used in Example 1, except that carbon black (BLACK PEARL L, prepared by CABOT CO.) was used instead of the complex compound obtained according to the above Preparation Example 3.

COMPARATIVE EXAMPLE 4

An ink composition was prepared according to the same method used in Example 1, except that carbon black (No. 25B, prepared by MITSUBISHI CO.) was used instead of the complex compound obtained according to the Preparation Example 3.

COMPARATIVE EXAMPLE 5

An ink composition was prepared according to the same method used in Example 1, except that using carbon black (No. 258, prepared by MITSUBISHI CO.) was used instead of the complex compound obtained according to the Preparation Example 3.

COMPARATIVE EXAMPLE 6

An ink composition was prepared according to the same method used in Example 1, except that carbon black (VAL-CAN XC-72R, prepared by CABOT CO.) was used instead of the complex compound obtained according to the Preparation Example 3.

COMPARATIVE EXAMPLE 7

An ink composition was prepared according to the same method used in Example 1, except for carbon black (CAB-O-JET 300, prepared by CABOT CO. and VALCAN XC-72R, prepared by CABOT CO.) was used instead of the complex compound obtained according to the Preparation Example 3.

The properties of the ink compositions prepared according to above Examples 1-8 and Comparative Examples 1-7 were measured according to the following methods.

(1) Long Term Storage Stability 100 ml of the ink compositions prepared according to above Examples 1-8 and Comparative Examples 1-7 were respectively placed into heat resistant vials; the opening of the vials was closed, and the vials were stored in an incubator at a temperature of 60° C. After remaining at this state for 2 months, the vials were examined, and it was determined whether precipitates were formed at the bottom of the vials.

It was found that, for the ink compositions prepared according to Examples 1-8 and Comparative Examples 1-7, precipitates were not formed, and from this result, it was determined that the ink compositions prepared according to Examples 1-8, which utilized metal complex coloring agents of the invention, had a similar storage stability compared with those prepared according to Comparative Examples 1-7, which utilized general coloring agents.

(2) Light Resistance Test

The ink compositions prepared according to Examples 1-8 and Comparative Examples 1-7 were placed into a SAMSUNG ELECTRONICS CO., LTD. ink cartridge, a 2 cm×2 cm solid pattern was printed on the cartridge, the resulting pattern was exposed to light in a Q-SUN Xenon Test Chamber for 100 hours, and then the change of OD value from before and after the test was determined. The results were evaluated as follows and are shown in Table 1.

$A = OD(\text{after test})/OD(\text{before test}) \times 100(\%)$ $O: A \geq 90$ $\Delta: 75 \leq A \leq 90$ $X: A \leq 75$

TABLE 1

| | Example | | | | | | | | Comparative Example | | | | | | |
|---|---|---|---|---|---|---|---|---|---|---|---|---|---|---|---|
| | 1 | 2 | 3 | 4 | 5 | 6 | 7 | 8 | 1 | 2 | 3 | 4 | 5 | 6 | 7 |
| Evaluation | o | o | o | o | o | o | o | o | o | Δ | o | x | Δ | Δ | o |

Table 1 shows that the light resistance of the compositions of Examples 1-8 is more effective than the light resistance of most of those of Comparative Examples 1-7 using ordinary coloring agents. Such results indicate that the light resistance was increased by using a metal complex formed by the coloring agent.

(3) Abrasion Resistance Test

The ink compositions prepared according to Examples 1-8 and Comparative Examples 1-7 were placed into a SAMSUNG ELECTRONICS CO., LTD. ink cartridge, a 2 cm×15 cm solid pattern was printed on the cartridge, the resulting patterns were dried for 24 hours, and then the degree to which the stains came out when scrubbing several times using a test device attached with cotton was observed. The results were evaluated as follows and are shown in Table 2.

O: little stain was observed

Δ: some stains came out on cotton

X: very deep stains came out on cotton.

TABLE 2

| | Example | | | | | | | | Comparative Example | | | | | | |
|---|---|---|---|---|---|---|---|---|---|---|---|---|---|---|---|
| | 1 | 2 | 3 | 4 | 5 | 6 | 7 | 8 | 1 | 2 | 3 | 4 | 5 | 6 | 7 |
| Evaluation | ○ | ○ | ○ | ○ | ○ | ○ | ○ | ○ | x | Δ | x | ○ | ○ | Δ | ○ |

Table 2 shows that the abrasion resistances of the compositions of Examples 1-8 are better than those of Comparative Examples 1-7, which include general coloring agents.

(4) Water Resistance Test

The ink compositions prepared according to Examples 1-8 and Comparative Examples 1-7 were placed into a SAMSUNG ELECTRONICS CO., LTD. ink cartridge, eight 0.5 cm×1.5 cm solid patterns were printed in a row on the cartridge, the resulting patterns were dried for 1 hour and fixed on a slanted place, and then distilled water was applied to papers above the patterns. The degree to which patterns were erased by the water was determined by measuring the changes in OD values before and after the test. The results are shown in Table 3.

$A = OD(\text{after test})/OD(\text{before test}) \times 100(\%)$ $O: A \geq 95$ $\Delta: 90 \leq A \leq 95$ $X: A < 90$

TABLE 3

| | Example | | | | | | | | Comparative Example | | | | | | |
|---|---|---|---|---|---|---|---|---|---|---|---|---|---|---|---|
| | 1 | 2 | 3 | 4 | 5 | 6 | 7 | 8 | 1 | 2 | 3 | 4 | 5 | 6 | 7 |
| Evaluation | ○ | ○ | ○ | ○ | ○ | ○ | ○ | ○ | Δ | Δ | x | ○ | Δ | Δ | ○ |

Table 3 shows that the water resistances of the compositions of Examples 1-8 are more effective than those of Comparative Examples 1-7 using general coloring agents.

The bipyridine-based metal complex compounds represented by formula (I) or (II) according to embodiments of the present invention may be used as described herein, as well as in combination with existing coloring agents to embody various colors and enhance durability such as light resistance, and the like. Because of this effect, the complex compounds according to embodiments of the present invention may be used as coloring agents in fibers, leathers, furs, papers, foodstuffs, medicines, cosmetics, paints, printing ink, ink-jet inks, plastic coloration, rubber coloration, furniture manufacturing, textile printing, paper manufacturing, cosmetics manufacturing, ceramic industry, and the like.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ink composition comprising an aqueous medium and a bipyridine-based metal complex represented by formula (I):

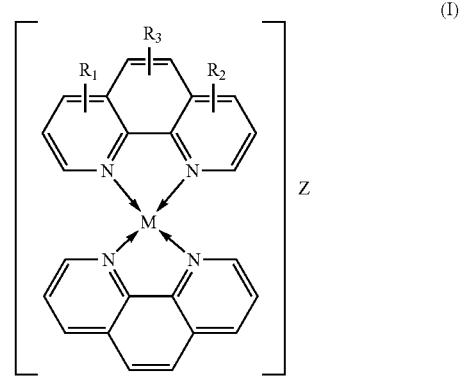

$R_1$, $R_2$, and $R_3$ are respectively mono-substituents, or the same or different multi-substituents, and are selected from the group consisting of a hydrogen atom, a halogen atom, a nitro group, —$SO_3H$, —COOH, a substituted or unsubstituted $C_1$-$C_{20}$ alkyl group, a substituted or unsubstituted $C_1$-$C_{20}$ heteroalkyl group, a hydroxy group, an amino group, a cyano group, a substituted or unsubstituted $C_2$-$C_{20}$ alkenyl group, a substituted or unsubstituted $C_1$-$C_{20}$ alkoxy group, a substituted or unsubstituted $C_1$-$C_{20}$ alkylsulfonamide group, a substituted or unsubstituted $C_6$-$C_{20}$ arylsulfonamide group, a substituted or unsubstituted $C_1$-$C_{20}$ acylamino group, a $C_1$-$C_{20}$ alkylureido group, a $C_6$-$C_{20}$ arylureido group, a $C_2$-$C_{20}$ alkoxycarbonyl group, a $C_2$-$C_{20}$ alkoxycarbonylamino group, a carbamoyl group, a sulfamoyl group, a sulfo group or its salt, a carboxy group or its salt, a substituted or unsubstituted $C_1$-$C_{20}$ hydroxyalkyloxyalkyl group, a substituted or unsubstituted $C_1$-$C_{20}$ dialkylaminoalkyl group, a substituted or unsubstituted $C_6$-$C_{20}$ pyridylalkyl group, a substituted or unsubstituted $C_5$-$C_{20}$ pyridyl group, a substituted or unsubstituted $C_6$-$C_{20}$ imidazolyl group, a hydrazine group, a hydrozone group, a substituted or unsubstituted $C_1$-$C_{20}$ pyridylalkyl group, a substituted or unsubstituted $C_6$-$C_{20}$ aryl group, a substituted or unsubstituted $C_6$-$C_{20}$ arylalkyl group, a substituted or unsubstituted $C_6$-$C_{20}$ heteroaryl group, or $C_6$-$C_{20}$ heteroarylalkyl group, a substituted or unsubstituted $C_6$-$C_{20}$ heteroarylalkenyl group, and a substituted or unsubstituted $C_3$-$C_{20}$ heterocycloalkyl group, wherein not all of $R_1$, $R_2$ and $R_3$ are a hydrogen atom;

M is a metal atom of one of groups III to XIV; and

Z is a counter ion.

2. The ink composition of claim 1, wherein the M has a positive charge of +1 to +5, and is at least one metal selected from the group consisting of silver (Ag), aluminum (Al), gold (Au), cerium (Ce), cobalt (Co), chromium (Cr), copper (Cu), europium (Eu), iron (Fe), germanium (Ge), indium (In), lanthanum (La), manganese (Mn), nickel (Ni), palladium (Pd), platinum (Pt), rhodium (Rd), ruthenium (Ru), scandium (Sc), silicon (Si), samarium (Sm), titanium (Ti), uranium (U), zinc (Zn) and zirconium (Zr).

3. The ink composition of claim 1, wherein Z may have a charge of −2, −1, 1 or 2, and is a negative ion selected from the group consisting of a halide ion, a sulfite ion, a $C_1$-$C_{10}$ alkyl sulfite ion, a sulfate ion, a $C_1$-$C_{10}$ alkyl sulfate ion, a nitrate ion, a nitrite ion, a perchloric acid ion, a $C_1$-$C_{10}$ alkylcarboxylate ion, a salicylate ion, a benzoate ion, a hexafluorophosphate ion and a tetrafluoroborate ion, or is positive ion selected from the group consisting of a lithium (Li) ion, a sodium (Na) ion, a potassium (K) ion, an ammonium ($NH_4$) ion and a phosphonium ion.

4. The bipyridine-based metal complex of claim 1, wherein at least one of $R_1$, $R_2$, and $R_3$ is selected from the group consisting of —OH, —$NH_2$, —COOH, —$SO_3$H, —$NO_2$, —F, —Cl, —Br and —I.

5. The bipyridine-based metal complex of claim 1, wherein the bipyridine-based metal complex of said formula (I) is represented by formula (VI) below:

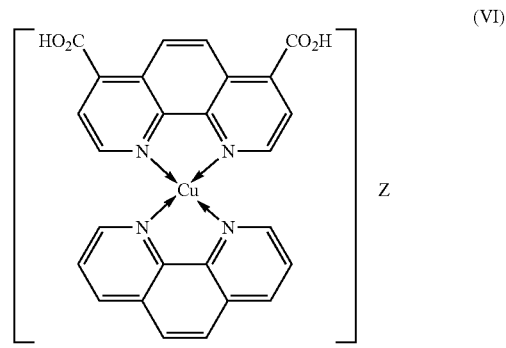

(VI)

wherein Z is a counter ion selected from among $(CH_3COO)_2$, $(SO_4)_2$, $(NO_3)_2$, $(CO_3)_2$, $(ClO_4)_2$, and $Cl_2$.

6. The ink composition of claim 1, comprising 0.1 to 10 parts by weight of the bipyridine-based metal complex based on 100 parts by weight of the aqueous liquid medium.

7. The ink composition of claim 1, wherein the ink composition includes 1 to 10,000 parts by weight of the coloring agent based on 100 parts by weight of the bipyridine-based metal complex.

8. The ink composition of claim 7, wherein the ink composition further includes 0.5 to 30 parts by weight of additives based on 100 parts by weight of coloring agent.

* * * * *